US008333927B2

(12) United States Patent
Ding et al.

(10) Patent No.: US 8,333,927 B2
(45) Date of Patent: Dec. 18, 2012

(54) HOLE JET REACTOR AND A PROCESS FOR THE PREPARATION OF AN ISOCYANATE USING THE REACTOR

(75) Inventors: Jiansheng Ding, Yantai (CN); Yong hua Shang, Yantai (CN); Deqiang Ma, Yantai (CN); Jingquan Hao, Yantai (CN); Peicheng Luo, Yantai (CN); Shuang Hu, Yantai (CN)

(73) Assignee: Ningbo Wanhua Polyurethanes Co., Ltd., Ningbo, Zhejiang Province (CN)

( * ) Notice: Subject to any disclaimer, the term of this patent is extended or adjusted under 35 U.S.C. 154(b) by 633 days.

(21) Appl. No.: 12/311,263

(22) PCT Filed: Aug. 21, 2007

(86) PCT No.: PCT/CN2007/002525
§ 371 (c)(1),
(2), (4) Date: Dec. 28, 2009

(87) PCT Pub. No.: WO2008/037173
PCT Pub. Date: Apr. 3, 2008

(65) Prior Publication Data
US 2010/0137634 A1    Jun. 3, 2010

(30) Foreign Application Priority Data

Sep. 28, 2006   (CN) .......................... 2006 1 0152393

(51) Int. Cl.
*B01J 19/00*   (2006.01)
*B01F 15/00*   (2006.01)
*B01F 15/02*   (2006.01)
*B01F 5/04*    (2006.01)
*B01F 5/06*    (2006.01)

(52) U.S. Cl. .................. 422/129; 366/150.1; 366/163.1; 366/167.1; 366/173.1; 366/173.2; 366/177.1; 366/178.1; 366/336; 366/340; 261/115; 261/116; 422/224

(58) Field of Classification Search .................. 422/129, 422/236, 224; 560/347, 338, 336, 330; 366/162.4, 366/167.1, 173.1, 173.2, 177.1, 178.1, 340, 366/150.1, 163.1, 164.1, 336; 261/75, 115, 261/116

See application file for complete search history.

(56) References Cited

U.S. PATENT DOCUMENTS
2,813,138 A  *  11/1957  MacQueen .................. 585/322
(Continued)

FOREIGN PATENT DOCUMENTS
CN           1304927           7/2001
(Continued)

OTHER PUBLICATIONS

International search report for corresponding int'l appln. No. PCT/CN2007/002525 dated Nov. 29, 2007.
(Continued)

*Primary Examiner* — Jennifer A Leung
*Assistant Examiner* — Natasha Young
(74) *Attorney, Agent, or Firm* — Ohlandt, Greeley, Ruggiero & Perle, L.L.P.

(57) ABSTRACT

The present invention relates to a hole-jetting type reactor and its applications, in particular to a process for the production of isocyanates by the phosgenation of aliphatic or aromatic diamines or triamines in the gas phase using this reactor. The present invention achieves a good mixing and reacting result of the gas-phase phosgenation reaction at a high temperature by improving the mixing of reactants in the reactor to reduce the possibility of forming swirls and eliminate negative pressure produced at a local jet area, which can finally reduce back-mixing and formation of solid by-products.

6 Claims, 1 Drawing Sheet

U.S. PATENT DOCUMENTS

| | | |
|---|---|---|
| 3,507,626 A | 4/1970 | Van Horn |
| 4,847,408 A | 7/1989 | Frosch et al. .................. 560/347 |
| 5,117,048 A | 5/1992 | Zaby et al. |
| 5,931,579 A | 8/1999 | Gallus et al. |
| 5,935,490 A * | 8/1999 | Archbold et al. ................ 261/76 |
| 6,082,891 A | 7/2000 | Schubert et al. .............. 366/338 |
| 2006/0153002 A1* | 7/2006 | Ryan .......................... 366/162.4 |
| 2010/0041914 A1* | 2/2010 | Woelfert et al. .............. 560/347 |

FOREIGN PATENT DOCUMENTS

| | | |
|---|---|---|
| CN | 1396152 | 2/2003 |
| CN | 1636972 | 7/2005 |
| CN | 1651406 | 10/2005 |
| CN | 1830540 | 9/2006 |
| EP | 0289840 | 11/1988 |
| GB | 1165831 | 10/1969 |
| WO | 2008/077287 A1 | 7/2008 |

OTHER PUBLICATIONS

Office Action dated Mar. 25, 2010 from EP 07 800 745.7-2104.

Office Action dated Mar. 11, 2010 from EP 07 800 745.7-2104.

* cited by examiner

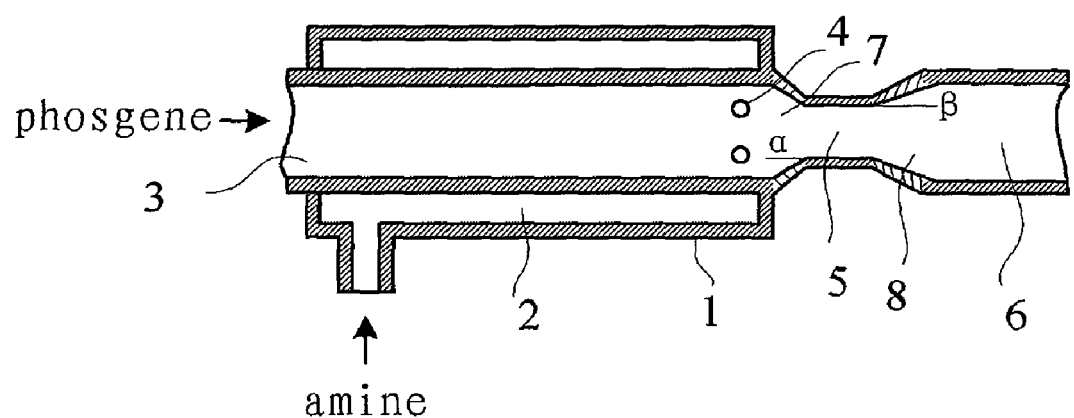

HOLE JET REACTOR AND A PROCESS FOR THE PREPARATION OF AN ISOCYANATE USING THE REACTOR

FIELD OF THE INVENTION

This invention relates to a hole-jetting type reactor and its applications, in particular, to a process for the production of isocyanates by the phosgenation of aliphatic or aromatic diamines or triamines in the gas phase using this reactor.

BACKGROUND OF THE INVENTION

The preparation of isocyanates by the reaction of amines with phosgene in the gas phase has been reported as early as in the 1940's (see Siefken, Annalen 562, 108, 1949). The phosgenation reaction is a fast reaction process and usually carried out in a tube reactor. The gas-phase phosgenation requires a fast mixing rate and simultaneously avoid blockage of the reactor under high temperature as far as possible.

GB 1,165,831 describes a process for the gas-phase phosgenation of amines in vapor form with phosgene is carried out at a temperature of 300° C. in a tube reactor equipped with mechanical stirrer, which can prevent a build-up of polymer by-products on the wall of the tube. However, the reactor requires considerable safety precaution.

EP 0,289,840 adopts a cylindrical reactor without any moving parts, in which the reactants are reacted with one another while a turbulent flow is maintained in the reactor. Because the gas-phase phosgenation of aliphatic amines is a very fast reaction process, the reaction result is controlled by the mixing rate. However, due to back-mixing of the reactants, isocyanates may react with amines to form solid deposit in the reactor, which may obstruct the gas flow.

U.S. Pat. No. 4,847,408 adopts a reactor where gaseous reactants are mixed and react under a strong turbulent flow state. The reactor is measured 2.5 mm in inner diameter and 17.5 mm in length. Phosgene and gaseous hexamethylene diamine heated to 400° C. are continuously introduced into a cylindrical reaction chamber where they are mixed together to produce HDI. CN 1,396,152 improves the reactor described in U.S. Pat. No. 4,847,408 by converting the cylindrical reactor into a venturi reactor in shape. The venturi reactor has a converged mixing chamber and the cross section of the reaction chamber is enlarged abruptly along the flow direction of the gaseous reactants. Such a design can reduce back-mixing and the contact of the gaseous mixture with the inside wall of the reactor.

U.S. Pat. No. 6,082,891 describes the manufacture of $H_6TDI$ with a good reaction result using a microchannel mixer. This microchannel mixer is composed of a series of superposed lamellas with etched microchannels, thickness of the lamella being about 100 µm, and the channel size on the lamella being of several tens µm. Each layer of the lamellas can only transport one kind of gaseous reactants, phosgene and the amine vapor pass the lamellas alternately. The gaseous reactants emerging from the microchannel mixer are rapidly mixed, meanwhile a dispersive or turbulent flow is maintained. Because the dispersive effect is enhanced before mixing, this type of mixer obtains a good mixing result. However, due to the small size of the channel, there is a risk that a polymer produced at a high temperature may block the channel.

It can be seen from the above comparison that the phosgenation reaction of amines in the gas phase is a fast reaction process. Polymer by-products may be produced if the mixing of the gaseous reactants is not efficient enough. Thus a high mixing rate is desired. It can also be seen from the prior art that the key to obtaining a good reaction result is to adopt a reactor with an excellent mixing efficiency while avoiding the production of solid by-products.

SUMMARY OF THE INVENTION

In order to overcome the weaknesses of the above-mentioned prior art, one objective of the present invention is to provide a newly designed hole-jetting type reactor, while another objective of the invention is to provide a process for the production of isocyanates by the phosgenation of amines in the gas phase using said reactor.

A hole-jetting type reactor provided according to the present invention comprises an internal feed tube, an external feed tube coaxial with the internal feed tube; wherein an annular space is defined between the two above-mentioned feed tubes; a convergent channel is coaxially connected to the downstream part of the internal feed tube; and a necking tube is coaxially connected with the convergent channel, wherein the cross sectional area of the necking tube is less than that of the internal feed tube; a divergent channel is coaxially connected to the downstream part of the necking tube; a reaction tube is coaxially connected with the divergent channel, wherein the cross sectional area of the reaction tube is greater than that of the necking tube; and the holes are made in the wall of the downstream part of the internal feed tube or in the wall of the convergent channel, and the holes are arranged on the same cross section of the internal feed tube or the convergent channel, wherein the cross section is perpendicular to the axis of the internal feed tube.

According to the hole-jetting type reactor of the present invention, the number of holes is 2 to 20, preferably 4 to 10. The shape of cross section of the holes may be a circle, an oval, a square, a rhombus, and so on.

According to the hole-jetting type reactor of the present invention, the total cross sectional areas of the holes amount to 2% to 30% of the cross sectional area of the internal feed tube, preferably 5% to 15% of the cross sectional area of the internal feed tube.

According to the hole-jetting type reactor of the present invention, it is preferred that the holes are arranged in the downstream part of the internal feed tube and are as close to the beginning of the convergent channel as possible, or are arranged in the wall of the convergent channel. Preferably, the holes are arranged in the wall of the downstream part of the internal feed tube, and the distance from the plane of the holes to the beginning of the convergent channel is in the range of about 0 to 5 cm, with the plane of the holes being perpendicular to the flow direction of the reactant in the internal feed tube; or are arranged in the wall of the convergent channel and distributed in the region from the beginning to the central cross section of the convergent channel.

According to the hole-jetting type reactor of the present invention, the angle α between the wall of the convergent channel 7 and the flow direction in the internal feed tube 3 is 30 to 60 degrees; and the angle β between the wall of the divergent channel 8 and the flow direction in the reaction tube 6 is 30 to 60 degrees; the length-diameter ratio of the necking tube is 1:1 to 15:1, preferably 3:1 to 10:1.

According to the hole-jetting type reactor of the present invention, the inner diameter of the necking tube is 0.2 to 0.8 times the inner diameter of the internal feed tube, preferably 0.4 to 0.7 times the inner diameter of the internal feed tube.

According to the hole-jetting type reactor of the present invention, the inner diameter of the reaction tube preferably equates to that of the internal feed tube.

According to the hole-jetting type reactor of the present invention, part or preferably all of the holes are arranged on the same cross section, wherein the cross section is perpendicular to the flow direction in the internal feed tube, and more preferably distributed symmetrically.

According to the present invention, the reactor can be used for the preparation of isocyanates by the phosgenation of amines in the gas phase. The reactor is generally made of steel, glass, or alloyed or enameled steel.

The present invention also provides a process for the production of isocyanates corresponding to the formula (I) with the corresponding amines represented by the formula (II) in the gas phase,

$$R(NCO)_n \quad\quad\quad (I)$$

$$R(NH_2)_n \quad\quad\quad (II)$$

Wherein R represents an aliphatic or aromatic hydrocarbon group with up to 15 carbon atoms, provided that there are at least two carbon atoms being arranged between the two NCO groups; and n is 2 or 3, The process comprises the following steps:

(a) heating an amine corresponding to formula (II) and phosgene to 200° C.-600° C.;

(b) making phosgene enter and flow in parallel through the internal feed tube of the reactor, and allowing the amine in vapor form to enter the external feed tube and pass through the holes so as to jet the amine into the phosgene stream perpendicularly to the flow direction of phosgene; and (c) making phosgene and the amine vapor, after being mixed, flow through the convergent channel, the necking tube and the divergent channel to enter the reaction tube to react.

Preferably, in the above-mentioned step (a), the amine may optionally be diluted with an inert gas or with the vapors of an inert solvent. The inert gas may be nitrogen or argon gas, and the inert solvent may be selected from the group consisting of toluene, xylene, o-dichlorobenzene and decalin.

In the process of the present invention, the velocity of phosgene before being mixed is at least 1 m/s, preferably 3 to 20 m/s; and the velocity of amine vapor at the exit of the holes is 6 to 120 m/s, preferably 20 to 100 m/s.

In the process of the present invention, the ratio of the velocity of the amine vapor at the exit of the holes to that of phosgene is 1:1 to 10:1, preferably 3:1 to 5:1.

In the process of the present invention, the pressures in the internal feed tube and the external feed tube are generally about 200 to 3000 mbar, and the pressure at the exit of the reaction tube is generally about 150 to 1500 mbar.

The amine adopted in the present invention and indicated by the general formula (II) may be selected from the following compounds: 1,4-diaminobutane, 1,6-diaminohexane, 1,4-diaminocyclohexane, 1-amino-3,3,5-trimethyl-5-aminomethyl-cyclohexane (IPDA), and 4,4'-diaminodicyclohexylmethane ($H_{12}$MDA). Suitable aliphatic triamine may be selected from the group consisting of 4-(aminomethyl)octane-1,8-diamine and triaminononane. Suitable aromatic amine can be selected from the group consisting of a mixture of 2,4-/2,6-toluene diamines with an isomer ratio of 80/20 to 65/35, 2,4-toluene diamines (TDA), diaminobenzene, naphthalenediamine, 2,4'-/4,4'-diamino diphenyl methane and the isomer mixture thereof, and preferably from the group consisting of 1,6-hexanediamine, IPDA, $H_{12}$MDA, triamino nonane, and the mixture of 2,4-/2,6-toluene diamine with an isomer ratio of 80/20 to 65/35 and TDA.

Examples of isocyanates which may be produced by the present invention include 1,6-diisocyanatohexane, isophorone diisocyanate (IPDI), 4,4'-dicyclohexyl methane diisocyanate ($H_{12}$MDI), toluene diisocyanate and nonane triisocyanate.

As for the gas-phase phosgenation reaction at a high temperature, solid particles once formed in the reactor will be carbonized and coked, and it is difficult to remove the coked substance simply by flushing with the reaction materials, because of the faster reaction rate than that of a liquid-phase reaction and the low kinetic energy of the reaction materials in the mixing reaction area of the reactor. Thus, it is desired to enhance the mixing effect and prevent solid particles formed due to back-mixing from blocking the reactor as well. The reactor of the present invention is provided with a mixing area with a convergent channel, a necking tube, and a divergent channel. This mixing area is similar to a venturi tube in shape. This structure can increase the gas velocity and avoid back-mixing or whirling of the reactants, thus avoiding buildup and deposition of solid particles. Particularly, the reactor of the present invention is provided with the convergent channel between the internal feed tube and the necking tube; and the holes are arranged at the downstream part of the internal feed tube and close to the beginning of the convergent channel as far as possible, or in the wall of the convergent channel. When amine stream is jetted into phosgene stream through the holes, such a structure can reduce the possibilities of forming swirls and eliminate negative pressure produced at local jet areas. As such, a good mixing and reacting result can be obtained in the gas-phase phosgenation reaction of the present invention by reducing back-mixing and avoiding the forming of solid by-products.

BRIEF DESCRIPTION OF THE DRAWING

FIG. 1 is a schematic drawing of a hole-jetting type reactor according to the present invention.

DETAILED DESCRIPTION OF THE INVENTION

The mixer-reactor of the present invention will be described in detail with the accompanying drawings and embodiments, but not limited to these embodiments, and may include any other publicly known changes within the scope of the claims of the present invention.

As shown in FIG. 1, the hole-jetting type reactor mainly comprises the following parts: an internal feed tube 3 and an external feed tube 2 coaxial with the internal feed tube 3; an annular space is defined between the above-mentioned two feed tubes; two ends of the external feed tube 2 are closed; a convergent channel 7 is coaxially connected to the downstream part of the internal feed tube 3; a necking tube 5 is coaxially connected to the convergent channel 7, and the cross sectional area of the necking tube 5 is less than that of the internal feed tube 3; a divergent channel 8 is coaxially connected to the downstream part of the necking tube 5; a reaction tube 6 is coaxially connected to the divergent channel 8, and the cross sectional area of the reaction tube 6 is greater than that of the necking tube 5; the holes 4 are made in the wall of the downstream part of the internal feed tube 3 or in the wall of the convergent channel 7, and the holes are arranged on the same cross section of the internal feed tube or the convergent channel, wherein the cross section is perpendicular to the axis of the internal feed tube.

The reactor 1, according to the present invention, is provided with a mixing area with the necking tube 5, in shape similar to a venturi tube. The cross section of the mixing area decreases before entering the necking tube, and increases after leaving the necking tube. This structure can increase the gas velocity and avoid back-mixing or whirling of the reactants, thus avoiding buildup and deposition of polymer by-products. All of the holes 4 are preferably arranged on the same cross section of the internal feed tube or the convergent channel, wherein said cross section is perpendicular to the flow direction of phosgene in the internal feed tube, and the holes 4 are more preferably distributed symmetrically. Owing to the novel design of the reactor, the contact of the desired product with other components can be avoided, thus the yield of the desired product may be increased and simultaneously the buildup of by-products be reduced. However, it is also feasible to deviate from the above-mentioned arrangement.

There is no special requirement on the inner diameter of the reaction tube. The inner diameter of the reaction tube is generally required to be greater than that of the necking tube, and may however be greater than, equal to or less than that of the internal feed tube, preferably being equal.

There is no special requirement on the thickness of the annular space (i.e. the inner radius of the external feed tube minus the outer radius of the internal feed tube). The thickness of the annular space is generally 0.1 to 0.8 times the inner diameter of the internal feed tube, preferably 0.2 to 0.6 times, and more preferably 0.2 to 0.4 times.

The phosgenation reaction proceeds in the above-mentioned reactor 1. The amine vapor, diluted with an inert gas or the vapors of an inert solvent, enters the internal feed tube 3 through the external feed tube 2 and the holes 4. Phosgene flows directly from the internal feed tube 3 into the reactor 1. The stream of gaseous amine is jetted perpendicularly into the phosgene stream through the holes 4. The gaseous amine is mixed, usually under a turbulent flow state, with the phosgene stream. The resulting gaseous mixture flows through the convergent channel 7, the necking tube 5 and the divergent channel 8 and enters the reaction tube 6, thus the corresponding isocyanate is obtained.

The amine vapor is jetted into the phosgene stream through the holes 4 perpendicularly to the flow direction of the phosgene stream. To ensure intensive mixing of the two streams, the jetting directions of all the holes 4 are preferably aimed at the axis of the internal feed tube 3. However, the present invention can still be carried out if not all of the holes 4 are directed to the axis of the internal feed tube 3.

Before feed into the reactor, amine is generally vaporized and heated to a temperature within the range of 200° C. to 600° C., preferably about 250° C. to 500° C. The amine vapor is generally diluted with an inert gas such as nitrogen and argon, or with the vapors of an inert solvent such as toluene, xylene, chlorobenzene, o-dichlorobenzene, and decahydronaphthalene. Phosgene is generally heated to a temperature within the range of 200° C. to 600° C., preferably about 250° C. to 500° C. The phosgene for phosgenation is generally used in excess, based on the mole quantity of amino group, with an access amount of phosgene of 25% to 350% of the theoretical quantity, preferably about 50% to 250%; and a mole ratio of inert gas or vapors of an inert solvent to amino group is generally 0.1:1 to 2:1, preferably 0.2:1 to 1:1.

During the phosgenation reaction, the pressure inside the feed tube is preferably 200 to 3000 mbar, and the pressure at the exit of the reaction tube of the reactor 150 to 1500 mbar. The velocity of the phosgene stream before being mixed is at least 1 m/s, preferably 3 to 20 m/s; and the velocity of the amine vapor at the exits of the holes is generally 6 to 120 m/s, preferably 20 to 100 m/s, which is ensured by maintaining an appropriate pressure difference.

The ratio of the velocity of the amine vapor at the exits of the holes to that of phosgene is generally 1:1 to 10:1, preferably 3:1 to 5:1.

The present invention will be described in detail below with reference to embodiments. It is to be understood that these embodiments are provided only for the purpose of illustration and that variations can be made therein by those skilled in the art without departing from the spirit and scope of the present invention.

EXAMPLE 1

Phosgene, heated to 360° C., flowed continuously into the reaction tube at a rate of 12 m/s through the internal feed tube. At the same time, a mixture, heated to 360° C., of 4,4'-diaminodicyclohexylmethane ($H_{12}$MDA) and nitrogen was jetted at the rate of about 42 m/s into the phosgene stream through 6 holes made in the wall of the internal feed tube. The mole ratio of $H_{12}$MDA:phosgene:nitrogen was 1:6:1. The jetting directions of the holes were all perpendicularly aimed at the axis of the internal feed tube, i.e. the center of the phosgene stream flow. The diameter of each of the holes was 1 mm; the internal feed tube was measured 8 mm in inner diameter and 2 mm in wall thickness; the inner diameter of the external feed tube was 16 mm (the thickness of the annular space was 2 mm); the necking tube was measured 5 mm in inner diameter and 20 mm in length; and the pressure inside the reaction tube was 400 mbar. The reactor was connected at the downstream part thereof with an isocyanate condensation stage, followed by a phosgene and hydrogen chloride absorption-and-decomposition tower. The vapors emerging from the reaction tube of the reactor were condensed by absorption into o-dichlorobenzene at a temperature of 140° C. to 150° C. The hydrogen chloride and excess phosgene were subsequently removed in the absorption tower. $H_{12}$MDI was recovered in pure form by distillation. The yield of $H_{12}$MDI was 97.8% of the theory.

EXAMPLE 2

Phosgene, heated to 360° C., flowed continuously into the reaction tube at the rate of 8 m/s through the internal feed tube. At the same time, a mixture, heated to 360° C., of $H_{12}$MDA and nitrogen was jetted at the rate of about 25 m/s into the phosgene stream through 4 holes made in the wall of the internal feed tube. The mole ratio of $H_{12}$MDA:phosgene:nitrogen was 1:6:1. The diameter of each of the holes was 2 mm; the internal feed tube was measured 12 mm in inner diameter and 2 mm in wall thickness; the inner diameter of the external feed tube was 18 mm; the necking tube was measured 5 mm in inner diameter and 20 mm in length; and the pressure inside the reaction tube was 400 mbar. The vapors emerging from the reaction tube of the reactor were condensed and separated under the process conditions of Example 1. The yield of $H_{12}$MDI was 97.6% of the theory.

COMPARATIVE EXAMPLE 1

Example 2 was repeated under the same conditions by substituting a central nozzle type reactor, composed of a central nozzle and an annular space, for the hole-jetting reactor to perform the reaction. The cross sectional area of the central nozzle was equal to the total cross sectional areas of the holes. The area of the annular space between the central nozzle and the wall of the tube reactor was equal to the cross sectional area of the internal feed tube in Example 1. The cross sectional area of the reaction tube connected with the rear part of the mixer used in the comparative example is equal to that of the reaction tube in Example 2. According to the central nozzle type reactor, a mixture of gaseous amine and nitrogen flowed into the mixing tube through the central nozzle, and phosgene was introduced into the mixing tube through the annular space. It was found that, according to analyses by gas chromatography, the content of HMDI in the solution was 99.08% (GC normalization), and the yield of HMDI was 97.4% of the theory.

EXAMPLE 3

Isophoronediamine (IPDA) was reacted with phosgene under the same process conditions of Example 1. The mole ratio of IPDA:phosgene:nitrogen was 1:6:1. The reactor was the same as that in Example 1. Before entering the reactor, phosgene and a mixture of IPDA and nitrogen were separately preheated to 310° C. The yield of IPDI was 98.6% of the theory.

What is claimed is:

1. A hole-jetting type reactor, comprising:
   an internal feed tube;
   an external feed tube coaxial with the internal feed tube, the external feed tube having two ends, wherein the internal feed tube and the external feed tube define an annular space therebetween, and wherein the two ends of the external feed tube are closed;
   a convergent channel coaxially connected to a downstream part of the internal feed tube;
   a necking tube coaxially connected with the convergent channel, wherein the cross sectional area of the necking tube is less than that of the internal feed tube;
   a divergent channel coaxially connected to the downstream part of the necking tube;
   a reaction tube coaxially connected with the divergent channel, wherein the cross sectional area of the reaction tube is greater than that of the necking tube; and
   2 to 20 holes in the wall of the downstream part of the internal feed tube or in the wall of the convergent channel,
   wherein part or all of the holes are arranged at the same cross section of the internal feed tube or the convergent channel, and
   wherein the cross section is perpendicular to the flow direction of a reactant in the internal feed tube, and distributed symmetrically, and
   wherein the cross sectional area of the holes totals 2% to 30% of the cross sectional area of the internal feed tube.

2. The hole-jetting type reactor according to claim 1, wherein the reactor comprises 4 to 10 holes, and the total cross sectional area of the holes is 5% to 15% of the cross sectional area of the internal feed tube.

3. The hole-jetting type reactor according to claim 2, wherein the holes are arranged in the wall of the downstream part of the internal feed tube and the distance from the plane of the holes to the beginning of the convergent channel is in the range of about 0 to 5 cm, with the plane of the holes being perpendicular to the flow direction of reactant in the internal feed tube; or
   wherein the holes are arranged in the wall of the convergent channel and distributed in the region from the beginning to the central cross section of the convergent channel.

4. The hole-jetting type reactor according to claim 1, wherein an angle α between the wall of the convergent channel and the flow direction of reactant in the internal feed tube is 30 to 60 degrees, and an angle β between the wall of the divergent channel and the flow direction of reaction materials in the reaction tube is 30 to 60 degrees; and the ratio of length to diameter of the necking tube is 1:1 to 15:1.

5. The hole-jetting type reactor according to claim 4, wherein the ratio of length to diameter of the necking tube is 3:1 to 10:1, and the inner diameter of the necking tube is 0.2 to 0.8 times the inner diameter of the internal feed tube.

6. The hole-jetting type reactor according to claim 5, wherein the inner diameter of the necking tube is 0.4 to 0.7 times the inner diameter of the internal feed tube, and the inner diameter of the reaction tube is equal to that of the internal feed tube.

* * * * *